United States Patent [19]

Edward, Jr.

[11] 4,435,975
[45] Mar. 13, 1984

[54] APPARATUS AND METHOD FOR CUTTING A FLAT SURFACE ON A METALLIC MEMBER

[75] Inventor: Robert M. Edward, Jr., The Woodlands, Tex.

[73] Assignee: J B Deveopment Corporation, The Woodlands, Tex.

[21] Appl. No.: 334,746

[22] Filed: Dec. 28, 1981

[51] Int. Cl.³ .............................................. G01N 3/40
[52] U.S. Cl. .......................................... 73/81; 73/78; 409/244; 409/277; 409/283
[58] Field of Search ................... 73/78, 79, 81, 82, 83; 409/244, 276, 277, 283, 250, 293, 296, 310, 329, 338

[56] References Cited

U.S. PATENT DOCUMENTS

| | | | |
|---|---|---|---|
| 78,880 | 6/1868 | Lemman | 83/824 |
| 2,259,840 | 10/1941 | Smith | 73/78 |
| 2,517,358 | 8/1950 | Seaman | 409/281 |
| 2,870,688 | 1/1959 | Bonnafe | 409/277 |
| 3,295,363 | 1/1967 | Delporte | 73/81 |
| 3,877,298 | 4/1975 | Narang | 73/81 |

Primary Examiner—Gerald Goldberg
Assistant Examiner—John E. Chapman, Jr.
Attorney, Agent, or Firm—Bill B. Berryhill

[57] ABSTRACT

Apparatus for cutting a flat surface on a metallic member may comprise: a frame assembly including a clamping device on which a metallic member may be placed for clamping the metallic member in a firmly fixed position; a broach frame mounted on the frame assembly for movement between a first position engageable by and against which the metallic member may be firmly clamped by the clamping device and a second position away from and not engageable by the metallic member when on the clamping device; a broach blade having cutting surfaces thereon carried by the broach frame for reciprocal movement, when the broach frame is in the first position, between a first terminal and a second terminal position for cutting a flat surface on the metallic member when clamped against the broach frame; and a power device mounted on the frame assembly and attached to the broach blade between the first and second terminal positions. Also disclosed is a method of production line hardness testing of metallic members utilizing the apparatus of the present invention.

18 Claims, 3 Drawing Figures

APPARATUS AND METHOD FOR CUTTING A FLAT SURFACE ON A METALLIC MEMBER

BACKGROUND OF THE INVENTION

1. Field of the Invention

The present invention pertains to apparatus for cutting metallic members. Specifically, the present invention pertains to broach apparatus suitable for cutting flat surface on a metallic member, specifically suitable for cutting a flat surface for engagement by hardness testing apparatus to determine the hardness of the metallic member.

2. Brief Description of the Prior Art

In the production and treatment of metallic goods, it is frequently desired to determine certain characteristics of the goods such as hardness. The hardness of such metallic goods can be measured by determining resistance to penetration. Several scales or standards of reference for hardness of materials have been developed over the years. Two of the most common scales or tests are the Rockwell hardness test and the Brinell hardness test.

In most hardness tests, a testing machine is provided capable of forcing a penetrating device against the material to be tested. Generally, in automatic readout testing, the material is first clamped against the testing machine with a force in excess of the loads to be applied during the test. During clamping, the penetrating device is recessed and out of contact with the material. Clamping eliminates distortion or movement of material prior to the test.

After the material is properly clamped, a preliminary or set load or force is applied to the penetrating device. Then a full load or force is applied to the penetrating device. The difference in penetration between the set load and the full load is measured by various means and correlated with standard scales to determine the hardness of the material.

In such hardness tests, it is extremely important that the surface of the material being tested be perfectly perpendicular to the load or force being applied through the penetrating device. This is no great problem with flat parts of specimens. However, on curved or rounded parts, such as pipe or other cylindrical members, this creats a problem. To assure that a flat surface is provided for testing, it is often necessary to cut a small flat surface on the surface of the pipe. This may be accomplished with a broach device or in other manners. However, if the flat surface is cut on the test specimen prior to placing in the test apparatus, it is often difficult to clamp the test specimen in place with the flat surface cut thereon being accurately placed and perpendicular to the position with respect to the penetrating force applied by the hardness tester. If the flat surface is not perpendicular to the testing force, the force vectors created by such a misalignment will result in inaccurate test measurements.

Furthermore, the cutting of flat surfaces on rounded members, such as pipe, during production results in substantial time delay of the production facilities. A flat surface must be accurately cut on the pipe and then the pipe accurately positioned in the testing device. Prior art methods and apparatus for performing these functions leave something to be desired in accuracy and results in substantial production line slow-down or delay.

SUMMARY OF THE PRESENT INVENTION

In the present invention, unique broaching apparatus is provided for cutting a flat surface on a metallic member such as pipe. The broaching apparatus may be utilized with hardness testing apparatus and actually attached to the frame of such apparatus. However, the cutting apparatus of the present invention can also be utilized independently. The apparatus of the present invention utilizes a frame assembly, whether the same one as the hardness testing apparatus or not, which includes a clamping device on which the metallic specimen may be placed for clamping in a permanently fixed position; a broach frame mounted on the frame assembly for movement between a first position engageable by and against which the metallic specimen may be firmly clamped by the clamping device and a second position away from and not engageable by the metallic specimen when on the clamping device; a broach blade having cutting surfaces thereon carried by the broach frame for reciprocal movement, when the broach frame is in the first position, between a first terminal position and a second terminal position for cutting a flat surface on the metallic specimen when clamped against the broach frame; and a power device mounted on the frame assembly and attached to the broach blade for moving the broach blade between the first and second terminal positions.

When utilized with hardness testing apparatus in which a hardness tester head is mounted on the frame assembly, production line hardness testing may be accomplished with a method comprising the steps of: placing one of the metallic specimens on the frame assembly and applying a first clamping force through the clamping device for firmly clamping the specimen against the broach assembly, the broach assembly being disposed below the tester head; cutting a flat surface on the specimen with the broach assembly; removing the first clamping force and displacing the broach assembly from below the tester head; raising the specimen to the tester head and applying a second clamping force through the clamping device for firmly clamping the speciment against the tester head; applying predetermined forces to the penetrator shaft for penetration of the metallic specimen, the axis of the penetrator shaft being perpendicular to the flat surface thereon; determining the amount of penetration of the metallic specimen by the penetrator shaft; and correlating the amount of penetration with the hardness of the metallic specimen. Thus, the broaching apparatus of the present invention may be utilized with and become an integral part of production line hardness testing so that very little time is lost in preparation of the metallic specimens for testing. The clamping device normally utilized for clamping the material against the hardness tester head may be also utilized for clamping the material against the broach assembly prior to cutting. After cutting, the broach assembly is displaceable from beneath the tester head so that the clamping device can then place the test specimen against the hardness tester head for hardness testing. This also assures that the flat surface cut on the metallic specimen is perpendicular to the test loads applied through the penetrator shaft of the tester head.

The broaching cutting apparatus of the present invention has several unique features. As already mentioned, it is mounted on a frame for movement from a working position to a non-working position. The broach blade and its bearing support is unique in that almost no friction is encountered in movement of the broach blade itself. The only significant friction encountered is the firction encountered in the actual broaching or cutting operation of the test specimen. Other unique bearing features are utilized in assuring that the broach blade remains in a perfectly aligned position. While the broaching or cutting apparatus of the present invention is particularly suitable for use with and as an integral part of a hardness testing operation, it can also be utilized in other broaching operations.

Even through the broaching apparatus of the present invention is unique in several aspects, it is relatively simple in construction and operation. Its accuracy in the intended working environments is great. Many other objects and advantages of the invention will be apparent from reading the specification which follows in conjunction with the accompanying drawings.

DESCRIPTION OF A PREFERRED EMBODIMENT

Figure 1:
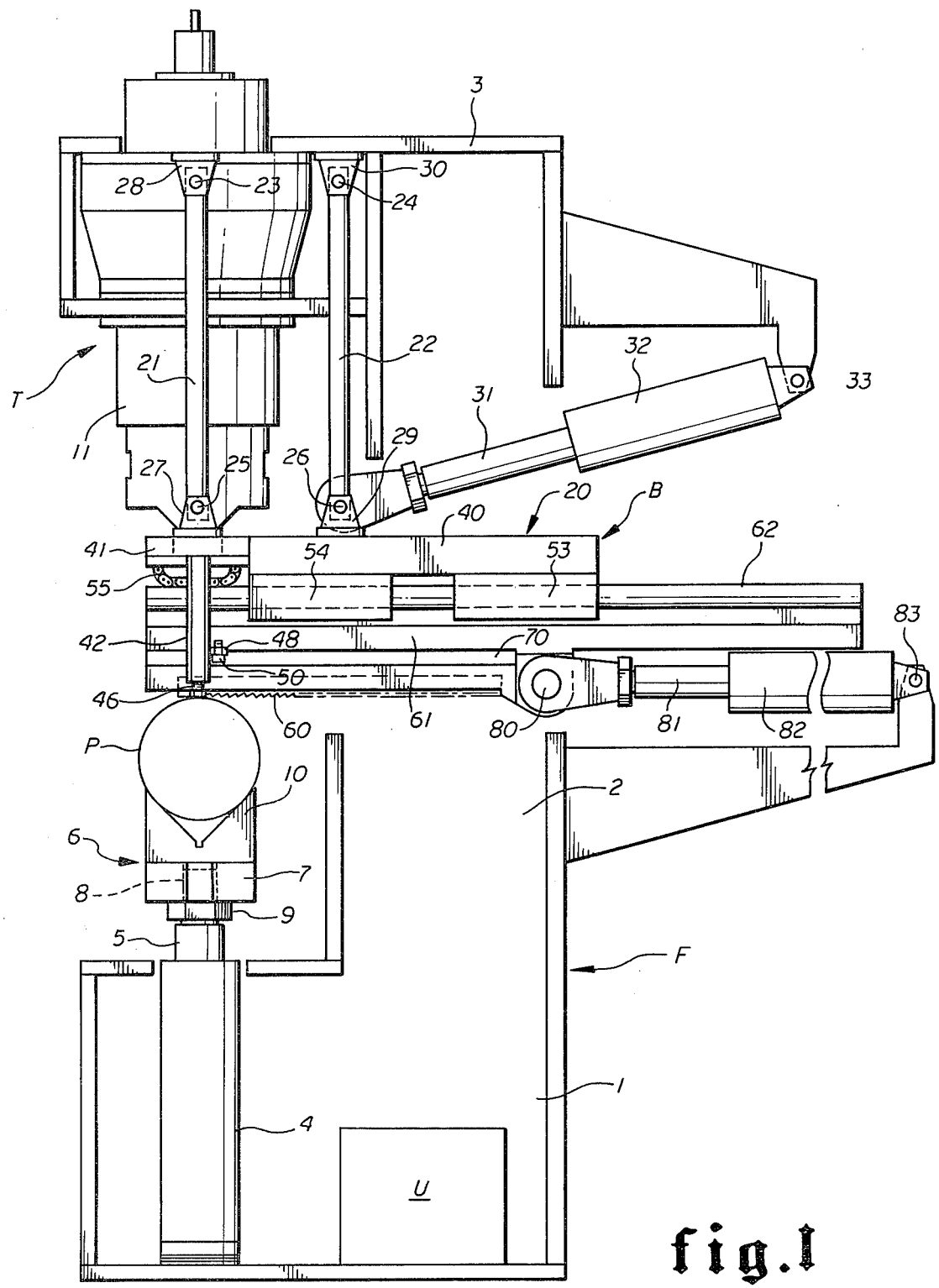
FIG. 1 is a side elevation view of broaching apparatus of the present invention being utilized with hardness testing apparatus.

Referring first to FIG. 1, there is shown apparatus for testing the hardness properties of pipe P utilizing apparatus according to a preferred embodiment of the invention for cutting a flat surface on the pipe for testing purposes. All of the testing apparatus and the broaching or cutting apparatus is supported on a frame or frame assembly F which includes a base section 1, a column section 2 and a cantilevered upper section 3. The frame assembly F may be made in any suitable manner. The one shown in FIG. 1 is of the C frame type which allows lateral introduction of the pipe or test member P into the assembly.

Supported in the base section 1 is a cylinder 4 in which is carried a piston (not shown) and from which extends a rod 5. The cylinder 4 may be connected to a source of fluid power, such as a hydraulic pump unit U, by which pressurized fluid may be applied to the piston for raising the rod 5. Attached to the upper end of rod 5 is a support assembly 6 on which the pipe P or other test specimen may be placed. In the particular embodiment shown, the support assembly 6 comprises a base plate 7 having a threaded hole 8 for threadedly receiving the correspondingly threaded end of rod 5. A lock nut 9 may also be provided. Mounted on top of the base plate 7 is a V block or cradle 10 on which the pipe specimen P is placed. Of course, if the pipe member P is of substantial length, the support assembly 6 may be relatively long or in the alternative a plurality of power cylinders and support assemblies may be provided at various longitudinal points along the pipe member P.

Supported on the frame assembly F and depending from the upper section 3 is a hardness tester head assembly T. The tester head assembly T includes a housing 11 in which is carried a reciprocal penetrator shaft (not shown) one end of which is adapted for contact with the metallic specimen or pipe member P. The tester head assembly T also includes operating means (not shown) for reciprocation of the penetrator shaft and for applying predetermined forces thereto. The tester head assembly T is fully described in copending Patent Application Ser. No. 334,747 filed concurrently herewith. For present purposes it is sufficient to known that when operated at the proper time the tester head assembly T provides predetermined forces to its penetrator shaft for penetration of the metallic specimen or pipe P resulting in a signal of some type indicative of the amount of penetration of the pipe P by the penetrator shaft.

Also carried by the frame assembly F is a broach assembly B which is the primary subject matter of the present invention. The broach frame 20 is supported on the frame assembly F by a plurality of support arms 21 and 22, the upper ends of which are pivotally attached by pins 23 and 24 to the frame assembly F and the lower ends of which are pivotally attached by pins 25 and 26, respectively, to the broach frame 20. As illustrated, there are two support arms 21 and one support arm 22. The pivot connections may be provided by brackets or clevis members 27, 28, 29 and 30, best illustrated for clevis members 27 in FIG. 3. Pins 23, 24, 25, and 26, which engage corresponding holes in the clevis members and support arms, actually provide the pivoted connection. Bearing members (not shown) may be placed in the holes of the support arms 21 and 22 to reduce friction of pivoting.

It will be noted that the support arms 21 and 22 are parallel to each other and of equal length. Connected at one of the pivot points 26 is the rod end 31 of a power cylinder 32, the opposite end of which is connected at 33 to another portion of the frame assembly F. It can be understood that if pressurized fluid is applied to the power cylinder 32 so as to cause the rod 31 to be retracted thereinto, the broach frame 20 and the entire broach assembly B will be caused to pivot about pivot points 23 and 24 in an arcuate path from a first position, as illustrated in FIG. 1, to a second position away from the tester head assembly T and pipe member P.

The broach frame 20 may include an elongated plate 40, to the upper side of which is welded or attached in any suitable manner the clevis member 29 and at one end of which may be a cross member 41 to which the clevis members 27 may be attached. Triangular shaped gusset members 42 and 43 (see FIG. 3) may be affixed to the cross member 41 for depending therefrom. The gusset members 42 and 43 may be provided with threaded holes 44 and 45 (see FIG. 3) from which extend threaded bolts or feet 46 and 47 (see FIG. 3) for contact with the test specimen or pipe P. Attached to gussets 42 and 43 are brackets 48 and 49 in which are thrust bearings engaged by rollers 50 and 51 (see FIGS. 1 and 3), the purpose of which will be more fully understood hereafter.

Attached to the lower side of the broach frame 20 is a pair of pillow block type bearings 53, 54 and two roundway type bearings 55, 56. When the broach assembly is in the first position illustrated in FIGS. 1, 2, and 3, the roundway type bearings 55 and 56 are directly above the pipe specimen P.

Figure 3:
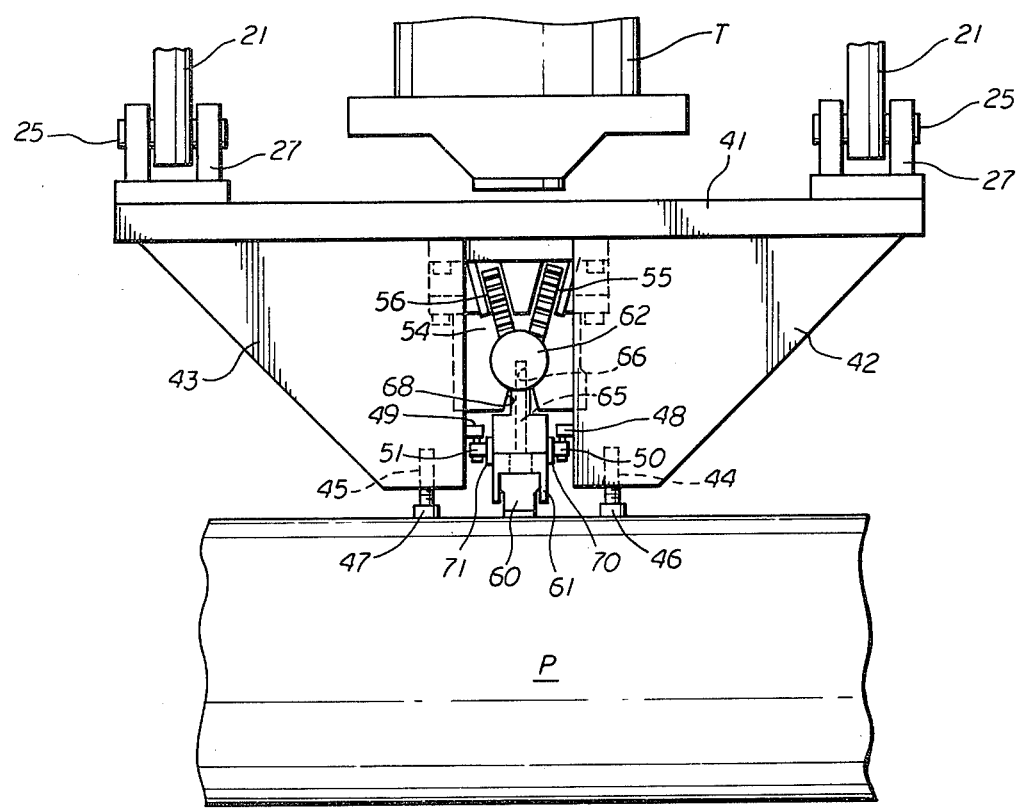
FIG. 3 is an end elevation view of the broaching apparatus of FIG. 2 as viewed along the lines 3—3 thereof.

Carried by the broach frame B is a broach blade 60, broach blade support member 61 and a bearing shaft 62. The bearing shaft 62 is supported in pillow blocks 53 and 54 for reciprocation therein. The roundway type bearings 55 and 56 radially bear against the bearing shaft 62. As best seen in FIG. 3, each of the bearings 55 and 56 bear against the bearing shaft 62 at equal and opposite angles from a vertical plane intersection the axis of the bearing shaft 62. The broach blade 60 is held in a bottom opening longitudinal recess of the broach blade support 61. The broach blade support 61 is connected to the bearing shaft 62 by cap screws 65 which extend through holes provided therefor for threaded engagement with tapped holes 66 in the bearing shaft. The broach blade support 61 is reduced in thickness near the pillow blocks 53 and 54 for longitudinal movement within longitudinal slots 68 in these pillow blocks. Longitudinal bearing strips 70 and 71 are attached to the broach blade support member 61 for engagement with the corresponding thrust rollers 50 and 51.

Figure 2:
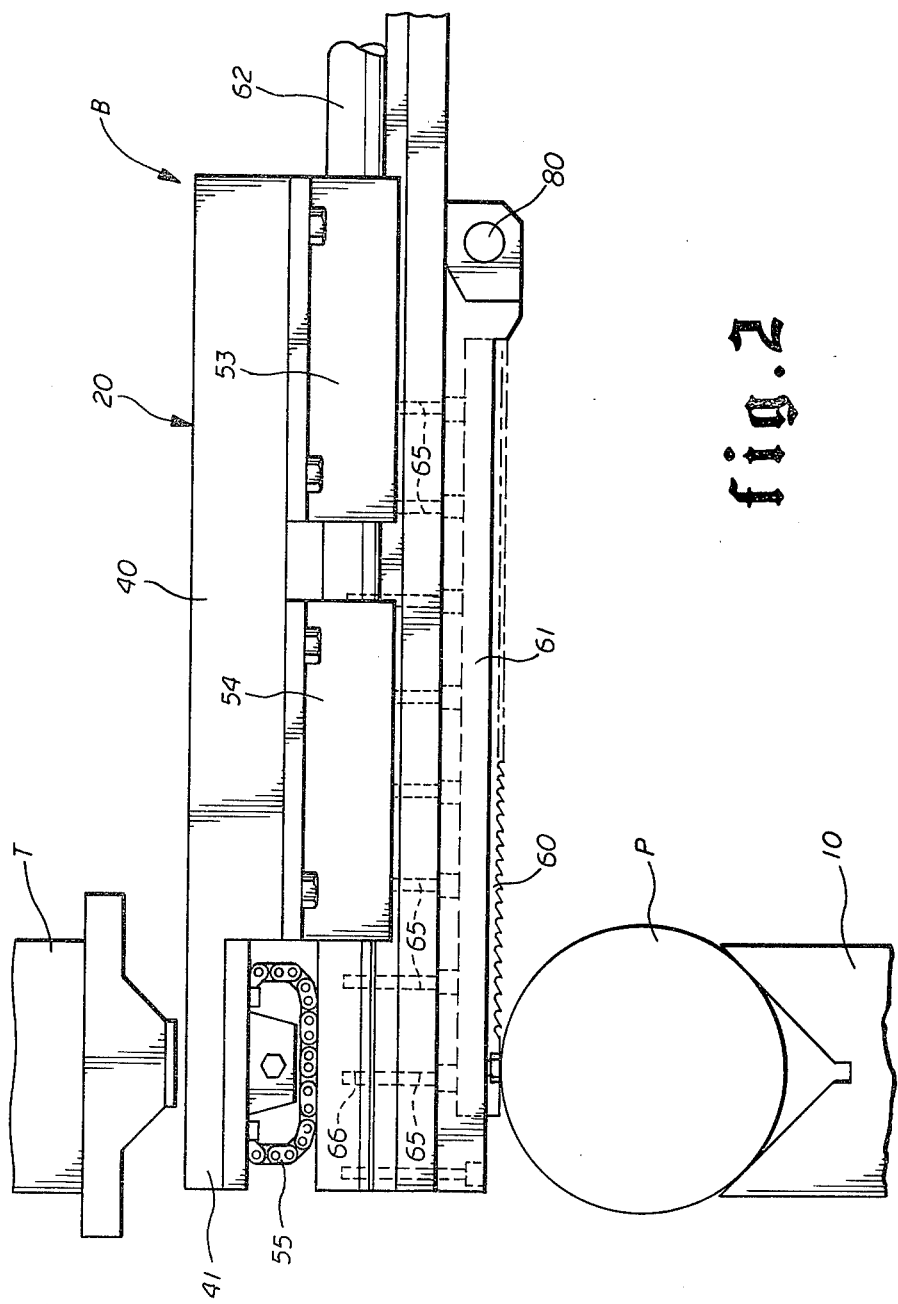
FIG. 2 is a side elevation view of the broaching apparatus of the present invention as shown in FIG. 1 but enlarged to show greater detail thereof.

Pivotally attached at 80 to the broach blade support 61 is the rod member 81 of a power cylinder 82. The power cylinder 82 is fixed at 83 to another portion of the frame assembly F. It can be understood that when the broach assembly B is in the first position shown in FIGS. 1 and 2, fluid power may be supplied to the power cylinder 82 causing the rod member 81 to extend and thereby moving the broach blade from a first terminal position (as shown in FIGS. 1 and 2) to a second terminal position in which the broach blade 60 moves transversely with respect to the pipe member P from left to right (as viewed in FIG. 1).

STATEMENT OF OPERATION

Referring now to all of the drawings, the broach assembly B of the present invention will be described for operation with the tester head assembly T for production line testing of pipe member P to determine the hardness thereof. This procedure is initiated with the broach assembly B in the first position shown in FIG. 1 and the broach blade 60 in the first terminal position shown in FIG. 1.

First a metallic specimen, in the exemplary embodiment pipe member P, is placed on the support block 10 with the clamping cylinder 4 fully retracted. With the pipe member P properly cradled, pressure is applied to the clamping cylinder 4 causing the pipe member P to be clamped against the positioning feet 46 and 47 of the broach assembly B. The pipe specimen P is firmly clamped against the broach assembly B, the broach assembly being disposed below the tester head assembly T.

Then fluid pressure is applied to the power cylinder 82 causing the rod member 81 to extend, moving the broach blade 60 from the first terminal position to the second terminal position, broaching or cuttings a flat surface recess on the upper side of the pipe member P. The broach blade 60 is then retracted to the first terminal position and clamping force applied by the clamping cylinder 4 is removed from the pipe member P. Then the entire broach assembly B is displaced from below the tester head assembly T by applying fluid pressure to cylinder 32 retracting the rod member 31 causing broach assembly B to pivot in an arcute path on its support arms 21 and 22.

Once the broach assembly B is cleared from between the pipe member P and the tester head assembly T, fluid pressure is again applied to the clamping cylinder 4 raising the pipe member P for direct contact with the tester head assembly T. A second and sufficient clamping force is applied through the clamping cylinder 4 for firmly clamping the pipe P against the tester head assembly T. As described in the aforementioned copending patent application Ser. No. 334,747, means may be provided for measuring the second clamping force and for controlling the amount of force applied against the tester head assembly T to a force greater than the forces applied by the tester head assembly T in the testing operation so that there will be no inaccuracies of readings due to deformation of the pipe member P.

After the pipe specimen P is firmly clamped in place, predetermined forces are applied to the penetrator shaft of the tester head assembly T by its operating means for penetration of the pipe member P, the axis of the penetrator shaft being perpendicular to the flat surface recess previously cut by the broach assembly B. The means for applying these predetermined forces are more fully described in the aforementioned copending patent application Ser. No. 334,747.

After the test forces are applied, the amount of the penetration of the pipe member P by the penetrator shaft is determined and correlated with the hardness of the pipe P. This may be done in a number of ways, one of which is described in copending patent application Ser. No 334,747.

After the hardness test is completed, the clamping force of the clamping cylinder 4 is relieved, allowing the pipe member P to be lowered and removed from the pipe support assembly 6. Another pipe member may then be placed on the support assembly 6 and the process repeated.

CONCLUSION

From the foregoing description, the unique broaching apparatus of the present invention provides a method of easily and quickly cutting a flat surface on a metallic test specimen which also lends itself to an improved and quicker method of production line hardness testing of metallic goods, especially pipe. The unique features of the broaching assembly result in accurate and efficient cutting as well as accurate testing, if utilized with testing apparatus.

While a single embodiment of the invention has been described herein, many variations thereof can be made without departing from the spirit of the invention. Accordingly, it is intended that the scope of the invention be limited only by the claims which follow.

I claim:

1. Apparatus for cutting a flat surface on and testing the hardness of a metallic member comprising:
   frame means including clamping means on which said metallic member may be placed for clamping said metallic member in a firmly fixed positon;
   tester head means mounted on said frame means in a fixed position directly above said clamping means;
   a broach frame mounted on said frame means for movement between a first position below said tester head means, above said metallic member and engageable by said metallic member and against which said metallic member may be firmly clamped by said clamping means and a second position away from said tester head means and not engageable by said metallic member when on said clamping means, allowing said metallic member to be firmly clamped against said tester head means by said clamping means;
   a broach blade having cutting means thereon carried by said broach frame for reciprocal movement, when said broach frame is in said first position, between a first terminal position and a second terminal position for cutting a flat surface on said metallic member when clamped against said broach frame; and power means mounted on said frame means and attached to said broach blade for moving said broach blade between said first and second terminal positions.

2. Apparatus as set forth in claim 1 in which said broach frame is supported on said frame means by a plurality of parallel support arms and the lower ends of which are pivotally attached to said broach frame allowing said broach frame to move in an arcuate path between said first and second positions.

3. Apparatus as set forth in claim 2 including second power means mounted on said frame means and attached to said broach frame for moving said broach frame between said first and second positions.

4. Apparatus as set forth in claim 1 in which said broach blade is an elongated member, the longitudinal axis of which is parallel to the path of said movement between said first and second terminal positions, said broach blade being supported by a broach blade support member attached to a bearing shaft which is engageable with a bearing assembly carried by said broach frame and the axis of which is parallel to said broach blade axis.

5. Apparatus as set forth in claim 4 in which said bearing assembly includes at least one pillow block type bearing.

6. Apparatus as set forth in claim 5 in which said at least one pillow block type bearing is provided with a longitudinal slot through awhich a portion of said broach blade support member extends for attachment to said bearing shaft.

7. Apparatus as set forth in claim 4 in which said bearing shaft is cylindrical and in which said bearing assembly includes at least one roundway type bearing radially bearing against said bearing shaft.

8. Apparatus as set forth in claim 7 in which said bearing assembly includes at least two of said roundway type bearings radially bearing against said bearing shaft at equal and opposite angles from a vertical plane intersecting the axis of said bearing shaft.

9. Apparatus as set forth in claim 4 including thrust bearing members carried by said broach frame bearing against the sides of said broach blade support member.

10. Apparatus as set forth in claim 4 in which said broach frame is supported on said frame means by a plurality of parallel support arms the upper ends of which are pivotally attached to said frame means, said broach frame being attached to second power means mounted on said frame means for moving said broach frame between said first and second positions.

11. A method of production line hardness testing of metallic specimens utilizing apparatus which includes a hardness tester head: a broach assembly; a frame for supporting said hardness tester head, said broach assembly and said metallic specimens to be tested; a clamping device for clamping said specimens against said broach assembly and said tester head; said tester head including a housing, a reciprocal penetrator shaft, one end of which is adapted for contact with said metallic specimens and operating means for reciprocation of said penetrator shaft and for applying predetermined forces thereto for penetration of said metallic specimens by said end of said penetrator shaft; said method comprising the steps of:

placing one of said metallic specimens on said frame and applying a first clamping force through said clamping device for firmly clamping said specimen against said broach assembly, said broach assembly being interposed between said tester head and said specimen;

cutting a flat surface on said specimen with said broach assembly;

removing said first clamping force and displacing said broach assembly from between said tester head and said specimen;

raising said specimen to said tester head and applying a second clamping force through said clamping device for firmly clamping said specimen against said tester head;

applying said predetermined forces to said penetrator shaft by said operating means of said penetration of said metallic specimen, the axis of said penetrator shaft being perpendicular to said flat surface thereon;

determining the amount of penetration of said metallic specimen by said penterator shaft end; and correlating said amoung of penetration with the hardness of said metallic specimen.

12. A method of hardness testing as set forth in claim 11 in which said metallic specimen is cylindrical in shape, said cylindrical specimen being disposed on said frame with its axis perpendicular to the axis of said tester head penetrator shaft, said cutting of a flat surface on said cylindrical specimen being accomplished with a broach blade the axis and movement of which is perpendicular to said cylindrical specimen axis.

13. A method of hardness testing as set forth in claim 12 in which said cylindrical specimen is prevented from rotation by said clamping device during said cutting of a flat surface thereon and for the remainder of said testing method so that said flat surface remains perpendicular to the axis of said tester head penetrator shaft throughout said testing method.

14. A method of hardness testing as set forth in claim 11 in which said tester head is provided with means for measuring said second clamping force and means for controlling the amount of force applied against said tester head, said second clamping force being a predetermined amount greater than said predetermined forces applied to said penetrator shaft by said operating means.

15. A method of hardness testing as set forth in claim 14 in which said predetermined forces applied to said penetrator shaft comprises a first predetermined force of relatively small magnitude and a subsequently applied second predetermined force of relatively greater magnitude, said determining the amount of penetration of said metallic specimens by said penetrator shaft being accomplished by measuring the difference in the depth of penetration of said metallic specimens by said penetrator shaft effected by said first and second predetermined forces.

16. A method of hardness testing as set forth in claim 15 in which said measuring the difference in depth penetrations of said metallic specimens is accomplished by an LVDT (linear voltage differential transducer) the armature of which is affixed to said tester head for simultaneous coaxial movement with said penetrator shaft.

17. A method of hardness testing as set forth in claim 16 in which said correlating said amount of penetration with the hardness of said metallic specimens is accomplished by electrical computer means connected to said LVDT for response to signals produced thereby.

18. A method of hardness testing as set forth in claim 14 in which said broach assembly is attached to said frame by pivoted support arms and attached to a power device by which said displacing of said broach assembly is accomplished by pivoting of said broach assembly on said support arms.

* * * * *